US008211427B2

(12) United States Patent
Kozian et al.

(10) Patent No.: US 8,211,427 B2
(45) Date of Patent: Jul. 3, 2012

(54) EGLN2 VARIANTS AND USE THEREOF IN PREVENTING OR TREATING THROMBOEMBOLIC DISORDERS AND CORONARY HEART DISEASES

(75) Inventors: Detlef Kozian, Kelkeim (DE); Matthias Herrmann, Hofheim (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 13/015,994

(22) Filed: Jan. 28, 2011

(65) Prior Publication Data

US 2011/0123515 A1 May 26, 2011

Related U.S. Application Data

(62) Division of application No. 12/089,627, filed as application No. PCT/EP2006/009518 on Sep. 30, 2006, now Pat. No. 8,114,398.

(30) Foreign Application Priority Data

Oct. 12, 2005 (DE) .......................... 10 2005 048 898

(51) Int. Cl.
*A61K 38/46* (2006.01)
*C12Q 1/68* (2006.01)
*C40B 30/06* (2006.01)
*C40B 30/00* (2006.01)

(52) U.S. Cl. ............ 424/94.6; 435/18; 435/6.1; 506/10; 506/7

(58) Field of Classification Search .................. None
See application file for complete search history.

(56) References Cited

U.S. PATENT DOCUMENTS

| | | | |
|---|---|---|---|
| 4,736,866 | A | 4/1988 | Leder et al. |
| 4,816,397 | A | 3/1989 | Boss et al. |
| 4,816,567 | A | 3/1989 | Cabilly et al. |
| 5,583,278 | A | 12/1996 | Alt |
| 5,625,122 | A | 4/1997 | Mak |
| 5,698,765 | A | 12/1997 | Mak |
| 5,744,305 | A | 4/1998 | Fodor et al. |
| 5,750,825 | A | 5/1998 | Yazaki et al. |

FOREIGN PATENT DOCUMENTS

| | | |
|---|---|---|
| EP | 0127839 | 5/1984 |
| EP | 0154133 | 9/1985 |
| EP | 0368684 | 5/1990 |
| EP | 0549721 | 4/1992 |
| EP | 0889723 | 3/1997 |
| EP | 0944398 | 6/1998 |
| EP | 0916336 | 5/1999 |
| EP | 0852493 | 9/2010 |
| WO | WO 88/01649 | 3/1988 |
| WO | WO 93/06213 | 4/1993 |
| WO | WO 98/24884 | 6/1998 |
| WO | WO 2004/058052 | 7/2004 |

OTHER PUBLICATIONS

Knowles et al (Novel mechanism of action for hydralazine: induction of hypoxia-inducible factor-1alpha, vascular endothelial growth factor, and angiogenesis by inhibition of prolyl hydroxylases). Cir. Res. Jul. 23, 2004; 95 (2):162-9. Epub Jun. 10, 2004.*

Alexander et al., Liposome mediated gene transfer and expression via the skin, Human Molecular Genetics, vol. 4, No. 12, 1995, pp. 2279-2285.

Appelhoff et al., Differential Function of the Prolyl Hydroxylases PHD1, PHD2, and PHD3 in the Regulation of Hypoxia-inducible Factor, J. of Biol. Chem., vol. 279, No. 7, Sep. 10, 2004, pp. 38458-38465.

Behr et al., Efficient gene transfer into mammalian primary endocrine cells with lipopolyamine-coated DNA, PNAS, Sep. 1989, vol. 86, pp. 6982-6986.

Branden et al., A peptide nucleic acid-nuclearl ocalization signal fusion that mediates nuclear transport of DNA, Nature Biotechnology, vol. 17, pp. 784-787, 1999.

Diamond et al., Monoclonal Antibodies, New England Journal of Medicine, vol. 304, No. 22, May 28, 1981, pp. 1344-1349.

Felgner et al., Enhanced Gene Delivery and Mechanism Studies with a Novel Series of Cationic Lipid Formulations, Journal of Biol. Chem., vol. 269, No. 4, Jan. 26, 1994, pp. 2550-2561.

Gossen et al., Inducible gene expression systems for higher eukaryotic cells, Current Opinion in Biotchnology, vol. 5, 1994, pp. 515-520.

Hengge et al., Expression of Naked DNA in Human, Pig and Mouse Skin, J. Clin. Invest. vol. 97, 1996, pp. 2911-2916.

Jaakkola et al., Targeting of HIF-alpha to the von Hippei-Lindau Ubiqutylation Complex by O2-Regulated Prolyl Hydroxylation, Science, vol. 292, Apr. 20, 2001, pp. 468-472.

Jackson, R.J., Cytoplasmic Regulation of mRNA Function: The Importance of the 3' Untranslated Region, Cell, vol. 74, Jul. 16, 1993, pp. 9-14.

Kichler et al., Influence of Membrane-Active Peptides on Lipospermine/DNA Complex Mediated Gene Transfer, Bioconjugate Chem. 1997, 8, 213-221.

Kozian et al., Comparative gene-expression analysis, TIBTECH, Feb. 1999, vol. 17, pp. 73-77.

Lee et al., Glucocorticoids regulate expression of dihydrofolate redutase cDNA in mouse mammary tumour virus chimaeric plasmids, Nature, vol. 294, Nov. 19, 1981, pp. 228-232.

Lindemann et al., Versatile Retrovirus Vector Systems for Regulated Gene Expression In Vitro and In Vivo, Molecular Medicine, vol. 3, 1997, pp. 466-476.

Mumberg, Dominik et al., Regulatable promotors of *Saccharomyces cerevisiae*: comparision of transcriptional activity and their use for heterologous expression, Nucleic Acid Research, (1994), vol. 22, No. 25, pp. 5767-5768.

Palmiter et al., Heterologous introns can enhance expression of transgenes in mice, PNAS, vol. 88, Jan. 1991, pp. 478-482.

(Continued)

*Primary Examiner* — Kagnew H Gebreyesus
(74) *Attorney, Agent, or Firm* — J. Darrell Fontenot

(57) ABSTRACT

The present invention refers to human EGLN2 variants having at position 58 of the amino acid sequence a serine or a leucine and their use in the prevention or treatment of thromboembolic or coronary heart diseases, in particular stroke, prolonged reversible ischemic neurological deficit (PRIND), transitoric ischemic attack (TIA), myocardial infarction and/or early myocardial infarction.

9 Claims, 5 Drawing Sheets

OTHER PUBLICATIONS

Plank et al., The influence of Endosome-disruptive Peptides of Gene Transfer Using Synthetic Virus-like Gene Transfer Systems, J. of Biol. Chem., vol. 269, No. 17, Apr. 29, 1994, pp. 12918-12924.

Russell et al., Nucleotide Sequence of the Yeast Alcohol Dehydrogenase II Gene, J. of Biol. Chem., vol. 258, No. 4, Feb. 25, 1983, pp. 2674-2682

Schwartz et al., Synthetic DNA-compacting peptides derived from human sequence enhance cationic lipid-mediated gene transfer in vitro and in vivo, Gene Therapy, vol. 6, 1999, pp. 282-292.

Shi, M.M., Technologies for Individual Genotyping, Detection of Genetic Polymorphisms in Drug Targets and Disease Genes, Am J. of Pharmacogenomics, vol. 2, No. 3, 2002, pp. 197-205.

Springer et al., VEGF Gene Delivery to Muscle: Potential Role for Vasculogenesis in Adults, Molecular Cell, vol. 2, 1988, pp. 549-558.

Takagi et al., A GPVI Polymorphism is a Risk Factor for Myocardial Infarction in Japanese, Atherosclerosis, Amsterdam, NL, vol. 165, 2002, pp. 397-398.

To et al., Suppresion of Hypoxia-Inducible Factor 1 (HIF-1) Transcriptional Activity by the HIF Prolyl Hydroxylase EGLN1, J. of Biol. Chem., Am Soc of Bio Chemists, vol. 280 No. 45, 2005, pp. 28102-38107.

Tuomainen et al., Increased Risk of Acute Myocardial Infarction in Carriers of the Hemochromatosis Gene CYS282TYR Mutation. A Prospective Cohort Study in Men in Eastern Finland, Circulation, Am Heart Assoc. vol. 100, Sep. 21, 1999, pp. 1274-1279.

Tuting et al., DNA Immunization Targeting the Skin: Molecule Control of Adaptive Immunity. Journal of Investigative Dermatology, vol. 111, 1996, pp. 183-188.

Wang et al., In vivo Gene Therapy with Interleukin-12 Inhibits Primary Vascular Tumour Growth and Induces Apoptosis in a Mouse Model, Journal of Investigative Dermatology, vol. 112, 1999, pp. 775-781.

Winter et al., Man-made antibodies, Nature, vol. 349, Jan. 24, 1991 pp. 293-299.

Wolf et al., Angiotensin II's Antiproliferative Effects Mediated Through AT2-Receptors Depend on Down Regulation of SM-20, Laboratory Investigation, vol. 82, No. 10, 2002, pp. 1305-1317.

Yu et al., Topical Gene Delivery to Murine Skin, J. of Invest. Dermatol., vol. 112, 1999, pp. 370-375.

Zhou et al., DNA transfection mediated by cationic liposomes containing lipopolylysine: characterization and mechanism of action, Biochimica et Biophysica Acta vol. 1189, 1994, pp. 195-203.

International Search Report for WO2007/042166 dated Apr. 19, 2007.

* cited by examiner

Figure 1

```
   1 gctttcccct gcctgcctgt ctctagtttc tctcacatcc cttttttttt ttcctttctc
  61 tagccaccct gaagggtccc ttcccaagcc cttagggacc gcagaggact tggggaccag
 121 caagcaaccc ccagggcacg agaagagctc ttgctgtctg ccctgcctca ccctgcccca
 181 cgccaggccc ggtggccccc agctgcatca agtggaggcg gaggaggagg cggaggaggg
 241 tggcaccatg ggcccgggcg gtgccctcca tgcccggggg atgaagacac tgctgccatg
 301 gacagcccgt gccagccgca gcccctaagt caggctctcc ctcagttacc agggtcttcg
 361 tcagagccct tggagcctga gcctggccgg gccaggatgg gagtggagag ttacctgccc
 421 tgtcccctgc tcccctccta ccactgtcca ggagtgccta gtgaggcctc ggcagggagt
 481 gggaccccca gagccacagc cacctctacc actgccagcc ctcttcggga cggttttggc
 541 gggcaggatg gtggtgagct gcggccgctg cagagtgaag gcgctgcagc gctggtcacc
 601 aagggggtgcc agcgattggc agcccagggc gcacggcctg aggcccccaa acggaaatgg
 661 gccgaggatg gtggggatgc cccttcaccc agcaaacggc cctgggccag gcaagagaac
 721 caggaggcag agcgggaggg tggcatgagc tgcagctgca gcagtggcag tggtgaggcc
 781 agtgctgggc tgatggagga ggcgctgccc tctgcgcccg agcgcctggc cctggactat
 841 atcgtgccct gcatgcggta ctacggcatc tgcgtcaagg acagcttcct gggggcagca
 901 ctgggcggtc gcgtgctggc cgaggtggag gccctcaaac ggggtgggcg cctgcgagac
 961 gggcagctag tgagccagag ggcgatcccg ccgcgcagca tccgtgggga ccagattgcc
1021 tgggtggaag gccatgaacc aggctgtcga agcattggtg ccctcatggc ccatgtggac
1081 gccgtcatcc gccactgcgc agggcggctg ggcagctatg tcatcaacgg cgcaccaag
1141 gccatggtgg cgtgttaccc aggcaacggg ctcgggtacg taaggcacgt tgacaatccc
1201 cacggcgatg ggcgctgcat cacctgtatc tattacctga atcagaactg ggacgttaag
1261 gtgcatggcg gcctgctgca gatcttccct gagggccggc ccgtggtagc caacatcgag
1321 ccactctttg accggttgct cattttctgg tctgaccggc ggaaccccca cgaggtgaag
1381 ccagcctatg ccaccaggta cgccatcact gtctggtatt tgatgccaa ggagcgggca
1441 gcagcaaag acaagtatca gctagcatca ggacagaaag gtgtccaagt acctgtatca
1501 cagccgccta cgcccaccta gtggccagtc ccagagccgc atggcagaca gcttaaatga
1561 cttcaggaga gccctgggcc tgtgctggct gctccttccc tgccaccgct gctgcttctg
1621 actttgcctc tgtcctgcct ggtgtggagg gctctgtctg ttgctgagga ccaaggagga
1681 gaagagacct ttgctgcccc atcatggggg ctggggttgt cacctggaca gggggcagcc
1741 gtggaggcca ccgttaccaa ctgaagctgg gggcctgggt cctaccctgt ctggtcatga
1801 ccccattagg tatggagagc tgggaggagg cattgtcact tcccaccagg atgcaggact
1861 tggggttgag gtgagtcatg gcctcttgct ggcaatgggg tgggaggagt accccaagt
1921 cctctcactc ctccagcctg aatgtgaag tgactcccca accccttttgg ccatggcagg
1981 caccttttgg actgggctgc cactgcttgg gcagagtaaa aggtgccagg aggagcatgg
2041 gtgtggaagt cctgtcagcc aagaaataaa agtttacctc agagctgcaa aaaaaaaaa
2101 aaaaaaaaaa a
```

Figure 2

MDSPCQPQPLSQALPQLPGSSSEPLEPEPGRARMGVESYLPCPLLPSYHCPGVPSEASAGSG
TPRATATSTTASPLRDGFGGQDGGELRPLQSEGAAALVTKGCQRLAAQGARPEAPKRKWAED
GGDAPSPSKRPWARQENQEAEREGGMSCSCSSGSGEASAGLMEEALPSAPERLALDYIVPCM
RYYGICVKDSFLGAALGGRVLAEVEALKRGGRLRDGQLVSQRAIPPRSIRGDQIAWVEGHEP
GCRSIGALMAHVDAVIRHCAGRLGSYVINGRTKAMVACYPGNGLGYVRHVDNPHGDGRCITC
IYYLNQNWDVKVHGGLLQIFPEGRPVVANIEPLFDRLLIFWSDRRNPHEVKPAYATRYAITV
WYFDAKERAAAKDKYQLASGQKGVQVPVSQPPTPT

Figure 3

MDSPCQPQPLSQALPQLPGSSSEPLEPEPGRARMGVESYLPCPLLPSYHCPGVPSEALAGSG
TPRATATSTTASPLRDGFGGQDGGELRPLQSEGAAALVTKGCQRLAAQGARPEAPKRKWAED
GGDAPSPSKRPWARQENQEAEREGGMSCSCSSGSGEASAGLMEEALPSAPERLALDYIVPCM
RYYGICVKDSFLGAALGGRVLAEVEALKRGGRLRDGQLVSQRAIPPRSIRGDQIAWVEGHEP
GCRSIGALMAHVDAVIRHCAGRLGSYVINGRTKAMVACYPGNGLGYVRHVDNPHGDGRCITC
IYYLNQNWDVKVHGGLLQIFPEGRPVVANIEPLFDRLLIFWSDRRNPHEVKPAYATRYAITV
WYFDAKERAAAKDKYQLASGQKGVQVPVSQPPTPT

Figure 4

```
   1 gctttcccct gcctgcctgt ctctagtttc tctcacatcc cttttttttt ttcctttctc
  61 tagccaccct gaagggtccc ttcccaagcc cttagggacc gcagaggact tggggaccag
 121 caagcaaccc ccagggcacg agaagagctc ttgctgtctg ccctgcctca ccctgcccca
 181 cgccaggccc ggtggccccc agctgcatca agtggaggcg gaggaggagg cggaggaggg
 241 tggcaccatg ggcccgggcg gtgccctcca tgcccggggg atgaagacac tgctgccatg
 301 gacagcccgt gccagccgca gcccctaagt caggctctcc ctcagttacc agggtcttcg
 361 tcagagccct tggagcctga gcctggccgg ccaggatgg gagtggagag ttacctgccc
 421 tgtcccctgc tcccctccta ccactgtcca ggagtgccta gtgaggcctt ggcagggagt
 481 gggaccccca gagccacagc cacctctacc actgccagcc ctcttcggga cggttttggc
 541 gggcaggatg gtggtgagct gcggccgctg cagagtgaag gcgctgcagc gctggtcacc
 601 aaggggtgcc agcgattggc agcccagggc gcacggcctg aggccccaa acggaaatgg
 661 gccgaggatg gtggggatgc cccttcaccc agcaaacggc cctgggccag gcaagagaac
 721 caggaggcag agcgggaggg tggcatgagc tgcagctgca gcagtggcag tggtgaggcc
 781 agtgctgggc tgatggagga ggcgctgccc tctgcgcccg agcgcctggc cctggactat
 841 atcgtgccct gcatgcggta ctacggcatc tgcgtcaagg acagcttcct gggggcagca
 901 ctgggcggtc gcgtgctggc cgaggtggag gccctcaaac ggggtgggcg cctgcgagac
 961 gggcagctag tgagccagag ggcgatcccg ccgcgcagca tccgtgggga ccagattgcc
1021 tgggtggaag gccatgaacc aggctgtcga agcattggtg ccctcatggc ccatgtggac
1081 gccgtcatcc gccactgcgc agggcggctg ggcagctatg tcatcaacgg gcgcaccaag
1141 gccatggtgg cgtgttaccc aggcaacggg ctcgggtacg taaggcacgt tgacaatccc
1201 cacggcgatg ggcgctgcat cacctgtatc tattacctga atcagaactg ggacgttaag
1261 gtgcatggcg gcctgctgca gatcttccct gagggccggc ccgtggtagc caacatcgag
1321 ccactctttg accggttgct catttttctgg tctgaccggc ggaacccccca cgaggtgaag
1381 ccagcctatg ccaccaggta cgccatcact gtctggtatt ttgatgccaa ggagcgggca
1441 gcagccaaag acaagtatca gctagcatca ggacagaaag gtgtccaagt acctgtatca
1501 cagccgccta cgcccaccta gtggccagtc ccagagccgc atggcagaca gcttaaatga
1561 cttcaggaga gccctgggcc tgtgctggct gctccttccc tgccaccgct gctgcttctg
1621 actttgcctc tgtcctgcct ggtgtggagg gctctgtctg ttgctgagga ccaaggagga
1681 gaagagacct tgctgccccc atcatggggg ctggggttgt cacctggaca ggggcagcc
1741 gtggaggcca ccgttaccaa ctgaagctgg gggcctgggt cctaccctgt ctggtcatga
1801 ccccattagg tatggagagc tgggaggagg cattgtcact tcccaccagg atgcaggact
1861 tggggttgag gtgagtcatg gcctcttgct ggcaatgggg tgggaggagt acccccaagt
1921 cctctcactc ctccagcctg gaatgtgaag tgactcccca accccttttgg ccatggcagg
1981 cacctttttgg actgggctgc cactgcttgg gcagagtaaa aggtgccagg aggagcatgg
2041 gtgtggaagt cctgtcagcc aagaaataaa agtttacctc agagctgcaa aaaaaaaaaa
2101 aaaaaaaaa a
```

EGLN2 VARIANTS AND USE THEREOF IN PREVENTING OR TREATING THROMBOEMBOLIC DISORDERS AND CORONARY HEART DISEASES

This application is Divisional application of U.S. patent application Ser. No. 12/089,627 filed Jan. 26, 2009 which is a 371 of International application no. PCT/EP2006/009518 filed on Sep. 30, 2006.

The present invention refers to human EGLN2 variants having at position 58 of the amino acid sequence a serine or a leucine and their use in the prevention or treatment of thromboembolic or coronary heart diseases, in particular stroke, prolonged reversible ischemic neurological deficit (PRIND), transitoric ischemic attack (TIA), myocardial infarction and/or early myocardial infarction.

EGLN2, due to its HIF prolyl hydroxylase activity also known as prolyl hydroxylase domain-containing protein 1 (PHD1), belongs to a group of closely related proteins of the Egl-Nine gene family which has a conserved genomic structure consisting of five coding exons. HIF (hypoxia-inducible factor) is a transcriptional regulator that plays a key role in many aspects of oxygen homeostasis but the contribution of the EGLN isoforms EGLN1 (PHD1), EGLN2 (PHD2) and EGLN3 (PHD3) to the physiological regulation of HIF is still uncertain (Appelhoff, R. J. et al. (2004) J. Biol. Chem., 279, 38458-38465, No. 37). It is reported that all EGLN isoforms show a differing cell specific and inducible behaviour, which should allow flexibility in the regulation of the HIF response to hypoxia. This would mean that specific pharmacological inhibition of a particular EGLN isoenzyme could have the potential for selective modulation of the HIF response that would be useful in therapeutic applications (Appelhoff, R. J. et al. (2004), supra). EGLN2 inhibition, for example, should activate the HIF response broadly across a range of cell types under resting conditions. In contrast specific inhibition of EGLN3 should selectively augment the response to hypoxia in certain tissues that express high levels of the enzyme (Appelhoff, R. J. et al. (2004), supra). This could open the possibility to treat ischemic/hypoxic diseases. Contrary to EGLN2 and EGLN3 not much is known for the physiological role of EGLN1.

In order to better understand a potential involvement of EGLN2 in the occurrence and progression of coronary heart diseases, genotype-phenotype association analyses have been carried out with a well characterized patient group with respect to a variation in the EGLN2 gene in position 470 of the EGLN2 reference sequence published under the reference number NM_053046.2 in accordance with the present invention. Different genetic variants of the EGLN2 gene are already known as SNPs (single nucleotide polymorphisms) and retrieved from the Internet: <URL:http://www.ncbi.nlm-.nih.gov/SNP/snp_ref.cgi?locusId=112398>.

Surprisingly it has been found that a variation of the nucleotide at position 470, in particular from cytosine to thymidine of a nucleic acid coding for the human EGLN2 protein or the amino acid at position 58, in particular from serine to leucine of the human EGLN2 protein correlates with the occurrence of thromboembolic and/or coronary heart diseases.

Therefore, a subject matter of the present invention relates to the EGLN2 protein containing an amino acid sequence according to SEQ ID NO: 3 and a nucleic acid coding for the EGLN2 protein, in particular a nucleic acid sequence according to SEQ ID NO: 4. Preferentially, the nucleic acids according to the present invention are DNA or RNA, preferably a DNA, in particular a double-stranded DNA. The sequence of the nucleic acids can furthermore be characterized in that it has at least one intron and/or one polyA sequence.

In a further embodiment of the invention, the nucleic acids can be used for the preparation of a vector, preferably in the form of a shuttle vector, phagemid, cosmid, expression vector or vector having gene therapy activity. Furthermore, knockout gene constructs or expression cassettes can be prepared using the nucleic acids described above. The expression vector can be a prokaryotic or a eukaryotic expression vector. Examples of prokaryotic expression vectors are, for expression in *E. coli*, e.g. the vectors pGEM or pUC derivatives, examples of eukaryotic expression vectors are for expression in *Saccharomyces cerevisiae*, e.g. the vectors p426Met25 or p426GAL1 (Mumberg et al. (1994) Nucl. Acids Res., 22, 5767-5768), for expression in insect cells, e.g. Baculovirus vectors such as disclosed in EP-B1-0 127 839 or EP-B1-0 549 721, and for expression in mammalian cells, e.g. the vectors Rc/CMV and Rc/RSV or SV40 vectors, which are all generally obtainable. In general, the expression vectors also contain promoters suitable for the respective host cell, such as, for example, the trp promoter for expression in *E. coli* (see, for example, EP-B1-0 154 133), the Met 25, GAL 1 or ADH2 promoter for expression in yeasts (Russel et al. (1983), J. Biol. Chem. 258, 2674-2682; Mumberg, supra), the Baculovirus polyhedrin promoter, for expression in insect cells (see, for example, EP-B1-0 127 839). For expression in mammalian cells, for example, suitable promoters are those which allow a constitutive, regulatable, tissue-specific or metabolically specific expression in eukaryotic cells. Regulatable elements according to the present invention are promoters, activator sequences, enhancers, silencers and/or repressor sequences. Examples of suitable regulatable elements which make possible constitutive expression in eukaryotes are promoters which are recognized by the RNA polymerase III or viral promoters, CMV enhancer, CMV promoter (also see Example 13), SV40 promoter or LTR promoters, e.g. from MMTV (mouse mammary tumour virus; Lee et al. (1981) Nature 214, 228-232) and further viral promoter and activator sequences, derived from, for example, HBV, HCV, HSV, HPV, EBV, HTLV or HIV. Examples of regulatable elements which make possible inducible expression in eukaryotes are the tetracycline operator in combination with a corresponding repressor (Gossen M. et al. (1994) Curr. Opin. Biotechnol. 5, 516-20). Examples of regulatable elements which make possible metabolically specific expression in eukaryotes are promoters which are preferably regulated by hypoxia.

In order to make possible the introduction of nucleic acids used according to the present invention and thus the expression of the polypeptide in a eu- or prokaryotic cell by transfection, transformation or infection, the nucleic acid can be present as a plasmid, as part of a viral or non-viral vector. Suitable viral vectors here are particularly: baculoviruses, vaccinia viruses, adenoviruses, adeno-associated viruses and herpesviruses. Suitable non-viral vectors here are particularly: virosomes, liposomes, cationic lipids, or poly-lysine-conjugated DNA.

Examples of vectors having gene therapy activity are virus vectors, for example adenovirus vectors or retroviral vectors (Lindemann et al., 1997, Mol. Med. 3: 466-76; Springer et al., 1998, Mol. Cell. 2: 549-58). Eukaryotic expression vectors are suitable in isolated form for gene therapy use, as naked DNA can penetrate into skin cells on topical application (Hengge et al., 1996, J. Clin. Invest. 97: 2911-6; Yu et al., 1999, J. Invest. Dermatol. 112: 370-5). Vectors having gene therapy activity can also be obtained by complexing the nucleic acid used according to the invention with liposomes, since a very high transfection efficiency, in particular of skin cells, can thus be achieved (Alexander and Akhurst, 1995, Hum. Mol. Genet. 4: 2279-85). In the case of lipofection, small unilamellar vesicles are prepared from cationic lipids by ultrasonic treatment of the liposome suspension. The DNA is bound ionically to the surface of the liposomes, namely in such a ratio that a positive net charge remains and the plasmid DNA is complexed to 100% of the liposomes. In addition to the lipid mixtures DOTMA (1,2-dioleyloxypropyl-3-trimethylammonium bromide) and DPOE (dioleoylphosphatidylethanolamine) employed by Felgner et al. (1987, supra), meanwhile numerous novel lipid formulations were synthesized and tested for their efficiency in the transfection of various cell lines (Behr, J. P. et al. (1989), Proc. Natl. Acad. Sci. USA 86, 6982-6986; Felgner, J. H. et al. (1994) J. Biol. Chem. 269, 2550-2561; Gao, X. & Huang, L. (1991), Biochim. Biophys. Acta 1189, 195-203). Examples of lipid formulations are DOTAP N-[1-(2,3-dioleoyloxy)propyl]-N,N, N-trimethyl-ammonium ethyl-sulphate or DOGS (TRANSFECTAM; diocta-decylamidoglycyl-spermine). Auxiliaries which increase the transfer of nucleic acids into the cell can be, for example, proteins or peptides which are bound to DNA or synthetic peptide-DNA molecules which make possible the transport of the nucleic acid into the nucleus of the cell (Schwartz et al. (1999) Gene Therapy 6, 282; Brandén et al. (1999) Nature Biotech. 17, 784). Auxiliaries also include molecules which make possible the release of nucleic acids into the cytoplasm of the cell (Planck et al. (1994) J. Biol. Chem. 269, 12918; Kichler et al. (1997) Bioconj. Chem. 8, 213) or, for example, liposomes (Uhlmann and Peymann (1990) supra). Another particularly suitable form of gene therapy vectors can be obtained by applying the nucleic acid used according to the invention to gold particles and shooting these into tissue, preferably into the skin, or cells with the aid of the so-called gene gun (Example 13; Wang et al., 1999, J. Invest. Dermatol., 112: 775-81, Tuting et al., 1998, J. Invest. Dermatol. 111: 183-8).

For gene therapy use of the nucleic acid described above, it is also advantageous if the part of the nucleic acid which codes for the polypeptide contains one or more non-coding sequences including intron sequences, preferably between promoter and the start codon of the polypeptide, and/or a polyA sequence, in particular the naturally occurring polyA sequence or an SV40 virus polyA sequence, especially at the 3' end of the gene, as a stabilization of the mRNA can be achieved thereby (Jackson, R. J. (1993) Cell 74, 9-14 and Palmiter, R. D. et al. (1991) Proc. Natl. Acad. Sci. USA 88, 478-482).

Knock-out gene constructs are known to the person skilled in the art, for example, from the U.S. Pat. No. 5,625,122; U.S. Pat. No. 5,698,765; U.S. Pat. No. 5,583,278 and U.S. Pat. No. 5,750,825.

The present invention further relates to a host cell which is transformed using a vector according to the invention or a knock-out gene construct. Host cells can be either prokaryotic or eukaryotic cells, examples of prokaryotic host cells are *E. coli* and examples of eukaryotic cells are *Saccharomyces cerevisiae* or insect cells. A particularly preferred transformed host cell is a transgenic embryonic non-human stem cell, which is characterized in that it comprises a knock-out gene construct according to the invention or an expression cassette according to the invention. Processes for the transformation of host cells and/or stem cells are well known to the person skilled in the art and include, for example, electroporation or microinjection.

Another subject matter of the present invention refers to a transgenic animal containing a nucleic acid or a vector according to the present invention.

Processes for the preparation of transgenic animals, in particular of the mouse, are likewise known to the person skilled in the art from DE 196 25 049 and U.S. Pat. No. 4,736,866; U.S. Pat. No. 5,625,122; U.S. Pat. No. 5,698,765; U.S. Pat. No. 5,583,278 and U.S. Pat. No. 5,750,825 and include transgenic animals which can be produced, for example, by means of direct injection of expression vectors (see above) into embryos or spermatocytes or by means of the transfection of expression vectors into embryonic stem cells (Polites and Pinkert: DNA Microinjection and Transgenic Animal Production, page 15 to 68 in Pinkert, 1994: Transgenic animal technology: a laboratory handbook, Academic Press, London, UK; Houdebine, 1997, Harwood Academic Publishers, Amsterdam, The Netherlands; Doetschman: Gene Transfer in Embryonic Stem Cells, page 115 to 146 in Pinkert, 1994, supra; Wood: Retrovirus-Mediated Gene Transfer, page 147 to 176 in Pinkert, 1994, supra; Monastersky: Gene Transfer Technology; Alternative Techniques and Applications, page 177 to 220 in Pinkert, 1994, supra). If nucleic acids used according to the invention are integrated into so-called targeting vectors (Pinkert, 1994, supra), it is possible after transfection of embryonic stem cells and homologous recombination, for example, to generate knockout mice which, in general, as heterozygous mice, show decreased expression of the nucleic acid, while homozygous mice no longer exhibit expression of the nucleic acid. Transgenic and knock-out cells or animals produced in this way can also be used for the screening and for the identification of pharmacologically active substances vectors having gene therapy activity.

Another subject matter of the present invention refers to an antibody specifically binding the EGLN2 protein containing an amino acid sequence according to SEQ ID NO: 3.

According to the present invention the term "specifically" means that the antibody binds to the EGLN2 protein containing an amino acid sequence according to SEQ ID NO: 3 but essentially not to the EGLN2 protein containing an amino acid sequence according to SEQ ID NO: 2, i.e. the antibody is suitable to differentiate between an EGLN2 protein having a serine at position 58 and an EGLN2 protein having a leucine at position 58.

This antibody is either polyclonal or monoclonal, preferably it is a monoclonal antibody. The term antibody is understood according to the present invention as also meaning antibodies or antigen-binding parts thereof prepared by genetic engineering and optionally modified, such as, for example, chimeric antibodies, humanized antibodies, multifunctional antibodies, bi- or oligospecific antibodies, single-stranded antibodies, F(ab) or F(ab)$_2$ fragments (see, for example, EP-B1-0 368 684, U.S. Pat. No. 4,816,567, U.S. Pat. No. 4,816,397, WO 88/01649, WO 93/06213, WO 98/24884).

The process to produce antibodies is carried out according to methods generally known to the person skilled in the art e.g. by immunizing a mammal, for example a rabbit, with the polypeptide described above or the mentioned parts thereof, if appropriate in the presence of, for example, Freund's adjuvant and/or aluminium hydroxide gels (see, for example, Diamond, B. A. et al. (1981) The New England Journal of Medicine, 1344-1349). The polyclonal antibodies formed in the animal as a result of an immunological reaction can then be easily isolated from the blood according to generally known methods and purified, for example, by means of column chromatography. Monoclonal antibodies can be produced, for example, according to the known method of Winter & Milstein (Winter, G. & Milstein, C. (1991) Nature, 349, 293-299). Recombinant antibodies can be produced as disclosed in the patent publications specified above.

Another subject matter of the present invention refers to a method for producing the EGLN2 protein containing an amino acid sequence according to SEQ ID NO: 3, wherein a cell as specified above is cultivated in a suitable culture medium and optionally the EGLN2 protein is isolated from the cell or the culture medium.

The EGLN2 protein is prepared, for example, by expression of the nucleic acid described above in a suitable expression system, as already explained above, according to the methods generally known to the person skilled in the art. Suitable host cells are, for example, the *E. coli* strains DH5, HB101 or BL21, the yeast strain *Saccharomyces cerevisiae*, the insect cell line *Lepidoptera*, e.g. from *Spodoptera frugiperda*, or the animal cells COS, Vero, 293, HaCaT, and HeLa, which are all generally obtainable. The EGLN2 protein can also be part of a fusion protein. Fusion proteins are prepared here as explained above which contain the polypeptides described above as, the fusion proteins themselves already having the function of a polypeptide as described above or the specific function being functionally active only after cleavage of the fusion portion. Especially included here are fusion proteins having a proportion of about 1-300, preferably about 1-200, in particular about 1-100, especially about 1-50, foreign amino acids. Examples of such peptide sequences are prokaryotic peptide sequences, which can be derived, for example, from the galactosidase of *E. coli*. Furthermore, viral peptide sequences, such as, for example, of the bacteriophage M13 can also be used in order thus to produce fusion proteins for the phage display process known to the person skilled in the art. Further preferred examples of peptide sequences for fusion proteins are peptides, that facilitate easier detection of the fusion proteins, these are, for example, "Green-Fluorescent-protein" or variants thereof.

For the isolation and/or purification of the proteins described above (a) further polypeptide(s) (tag) can be attached. Suitable protein tags allow, for example, high-affinity absorption to a matrix, stringent washing with suitable buffers without eluting the complex to a noticeable extent and subsequently targeted elution of the absorbed complex. Examples of the protein tags known to the person skilled in the art are a $(His)_6$ tag, a Myc tag, a FLAG tag, a haemaglutinin tag, glutathione transferase (GST) tag, intein having an affinity chitin-binding tag or maltose-binding protein (MBP) tag. These protein tags can be situated N- or C-terminally and/or internally.

A further subject matter of the present invention refers to a method of screening a modulator of an EGLN2 protein, wherein the method comprises the steps of:
(a) providing the EGLN2 protein or the nucleic acid coding for the EGLN2 protein,
(b) providing a test compound, and
(c) measuring or detecting the influence of the test compound on the EGLN2 protein or the EGLN2 gene.

In general, the EGLN2 protein or the nucleic acid coding for the EGLN2 protein is provided e.g. in an assay system and brought directly or indirectly into contact with a test compound, in particular a biochemical or chemical test compound, e.g. in the form of a chemical compound library. Then, the influence of the test compound on the EGLN2 protein or the nucleic acid coding for the EGLN2 protein is measured or detected. Thereafter, suitable modulators, e.g. activators or inhibitors, can be analyzed and/or isolated. For the screening of chemical compound libraries, the use of high-throughput assays are preferred which are known to the skilled person or which are commercially available.

According to the present invention the term "chemical compound library" refers to a plurality of chemical compounds that have been assembled from any of multiple sources, including chemically synthesized molecules and natural products, or that have been generated by combinatorial chemistry techniques.

In general, the influence of the test compound on EGLN2 or the EGLN2 gene is measured or detected in a heterogeneous or homogeneous assay. As used herein, a heterogeneous assay is an assay which includes one or more washing steps, whereas in a homogeneous assay such washing steps are not necessary. The reagents and compounds are only mixed and measured.

Suitable functional assays may be based on the gene expression of EGLN2, the direct activation or inhibition of EGLN2. In the presence of a biochemical or chemical compound to be tested as a modulator of EGLN2 gene expression, the direct activation or inhibition or the complex formation with other proteins, e.g. cellular proteins, can be measures by means generally known to a skilled person or as described in Appelhoff, R. J. et al. (2004), supra and/or Jaakkola, P. et al. (2001) Science, 292, 468-472, No. 5516.

For example, the prolyl hydroxylase activity can be measured by mass spectrometric analysis whereby the oxidization of Pro, e.g. $Pro^{564}$ of the prolyl hydroxylase or of the HIF-1α subunit can be detected, or by enzymatic assays known to a person skilled in the art, e.g. in an in vitro test assay and/or an in vitro whole cell test assay with human cells, animal cells, bacterial cells or yeast cells.

The solid phase-bound polypeptides can also be part of an array. Methods for preparing such arrays using solid phase chemistry and photolabile protecting groups are disclosed, for example, in U.S. Pat. No. 5,744,305. These arrays can also be brought into contact with test compound or compound libraries and tested for interaction, for example binding or changing conformation.

In another embodiment of the present invention, the method is carried out using whole cells. Usually cells growing at the bottom of multiwell plates are fixed and permeabilized, blocked and incubated with e.g. a primary (P)-specific antibody against the substrate of interest. Then, e.g. Europium labelled or HRP conjugated secondary antibodies in conjunction with specific chemiluminescent or colorimetric substances, e.g. as described above, are utilized to generate the signal. In combination with the use of a microscope not only the amount of (P)-specific antibodies can be quantified on the single cell level, but also phosphorylation-induced translocations of a substrate or morphological changes of the cells.

Advantageously the method of the present invention is carried out in a robotics system e.g. including robotic plating and a robotic liquid transfer system, e.g. using microfluidics, i.e. channeled structured.

In another embodiment of the present invention, the method is carried out in form of a high-through put screening system. In such a system advantageously the screening method is automated and miniaturized, in particular it uses miniaturized wells and microfluidics controlled by a roboter.

Another subject matter of the present invention refers to the use of an EGLN2 protein containing an amino acid sequence according to SEQ ID NO: 2 or 3 or of an nucleic acid coding for the EGLN2 protein for the production of a medicament for the prevention or treatment of thromboembolic and/or coronary heart diseases. Particularly the thromboembolic disease is, stroke, prolonged reversible ischemic neurological deficit (PRIND) and/or transitoric ischemic attack (TIA). Further, the coronary heart disease is particularly a myocardial infarction. Specifically, the EGLN2 protein containing an amino acid sequence according to SEQ ID NO: 3 or an nucleic acid coding for the EGLN2 protein is used for the production of a medicament for the prevention or treatment of stroke, PRIND and/or TIA and the EGLN2 protein containing an amino acid sequence according to SEQ ID NO: 2 or an nucleic acid coding for the EGLN2 protein is used for the production of a medicament for the prevention or treatment of myocardial infarction, in particular early myocardial infarction.

In detail, if the nucleotide at position 470 is thymidine in the chromosomal DNA or uracile in the mRNA or the amino acid at position 58 is leucine there exists a higher risk of stroke, PRIND and/or TIA. If, however, the nucleotide at position 470 is cytidine or the amino acid at position 58 is serine there exists a higher risk for a myocardial infarction, in particular early myocardial infarction.

According to the present invention, the term "EGLN2-C470C" refers to the group of persons which have cytidine on both alleles of the gene coding for EGLN2 at position 470 of the reference sequence NM_053046.2 which leads to the amino acid serine at position 58 of the corresponding protein. These persons are homozygous with respect to this EGLN2 variant. Consequently, the term "EGLN2-C470T" refers to the group of persons which have cytidine on one allele of the gene coding for EGLN2 which leads to serine at position 58 of the corresponding protein and thymidine on the other allele of the gene coding for EGLN2 which leads to leucine at position 58 of the corresponding protein. These persons are heterozygous with respect to this EGLN2 variant.

The nucleic acid sequence of the reference sequence coding for the human EGLN2 protein preferably has the nucleic acid sequence of SEQ ID NO: 1 and the amino acid sequence of the human EGLN2 protein preferably has the amino acid sequence of SEQ ID NO: 2. However, the present invention encompasses also other variants of human EGLN2 and the non-human homologs thereof, as for example other mammalian EGLN2 homologs or the EGLN2 homologs from *Caenorhabdidis elegans*, mouse or rat, provided that there is a nucleotide exchange from cytidine to thymidine at the position corresponding to position 470 of said reference sequence and/or an amino acid exchange from serine to leucine at the position corresponding to position 58 of said reference sequence and further provided that the corresponding protein has a prolyl hydroxylase activity, in particular a HIF prolyl hydroxylase activity. Said enzyme activity can be measured for example by mass spectrometric analysis as already explained above.

Generally, the specific nucleotide at position 470 can be determined by a nucleic acid sequencing method, a mass spectrometric analysis of the nucleic acid, a hybridisation method and/or an amplification method. Examples of a nucleic acid sequencing method are pyrosequencing and/or sequencing with the help of radioactive and/or fluorescence labelled nucleotides. Examples of the hybridisation method are Southern blot analysis, Northern blot analysis and/or a hybridisation method on a DNA-microarray. Examples of an amplification method are a TaqMan analysis, a differential RNA display analysis and/or a representational difference analysis (Shi M. M. (2002) Am J Pharmacogenomics., 2 (3), 197-205; Kozian & Kirschbaum (1999) Trends Biotechnol., 17 (2), 73-8.)

Furthermore, the amino acid sequence at position 58 can be determined by a method measuring the amount of the specific protein and/or a method measuring the activity of the specific protein. Examples of a method for measuring the amount of the specific protein are a Western blot analysis and/or an ELISA. Examples for measuring the activity of the specific protein are an in vitro test assay and/or an in vitro whole cell test assay with human cells, animal cells, bacterial cells or yeast cells, all known to a person skilled in the art.

Examples of a sample for the detection of the respective variant are a cell, a tissue or a body fluid, in particular in cellular components of the blood, endothelial cells or smooth muscle cells. Preferably the sample is pre-treated by conventional methods known to a person skilled in the art in order to isolate and/or purify the nucleic acids or chromosomal DNA, or the proteins of the sample for the further analysis.

A preferred method for the identification of a variant in accordance with the present invention contains the following steps:
(a) isolating a nucleic acid probe, in particular a DNA probe from a sample, in particular from a cell, tissue, body fluid, a cellular component of the blood, endothelial cells or smooth muscle cells, e.g. from a person or patient that should be investigated;
(b) amplifying the specific region encompassing position 470 of the ENGL2 gene with the help of primers, in particular the primers as specified in the Examples;
(c) sequencing the amplified region; and
(d) analysing the sequenced region.

An alternative method for the determination of a variant in accordance with the present invention contains the following steps:
(a) isolating the ENGL2 protein from a sample, in particular from a cell, tissue, body fluid, a cellular component of the blood, endothelial cells or smooth muscle cells, e.g. from a person or patient that should be investigated; and
(b) determining the amino acid at position 58 of the EGLN2 protein.

More preferred steps are individually or collectively specified in the Examples and are incorporated hereby by reference to each step.

Finally, the subject matter of the present invention refers to a method for producing a medicament for the treatment of thromboembolic and/or coronary heart diseases, wherein the method comprises the steps of:
(a) carrying out the screening method described above,
(b) isolating a measured or detected test compound suitable for the treatment of a thromboembolic and/or coronary heart diseases, and
(c) formulating the measured or detected test compounds with one or more pharmaceutically acceptable carriers or auxiliary substances.

According to step (c) of the above method the detected test compound is usually formulated with one or more pharmaceutically acceptable additives or auxiliary substances, such as physiological buffer solution, e.g. sodium chloride solution, demineralized water, stabilizers, $\epsilon$-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the medicament is in general adjusted using a suitable organic or inorganic buffer, such as, for example, preferably using a phosphate buffer, tris buffer (tris (hydroxymethyl)aminomethane), HEPES buffer ([4-(2-hydroxyethyl)piperazino]-ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The medicament can be administered in a conventional manner, e.g. by means of oral dosage forms, such as, for example, tablets or capsules, by means of the mucous membranes, for example the nose or the oral cavity, in the form of dispositories implanted under the skin, by means of injections, infusions or gels which contain the medicaments according to the invention. It is further possible to administer the medicament topically and locally in order to treat the particular joint disease as described above, if appropriate, in the form of liposome complexes. Furthermore, the treatment can be carried out by means of a transdermal therapeutic system (US), which makes possible a temporally controlled release of the medicaments. US are known for example, from EP 0 944 398 A1, EP 0 916 336 A1, EP 0 889 723 A1 or EP 0 852 493 A1.

Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The following Figures, Tables, Sequences and Examples shall explain the present invention without limiting the scope of the invention.

DESCRIPTION OF THE FIGURES

FIG. 1 shows the nucleic acid sequence of the human EGLN2 gene with the NCBI number NM_053046. The primers used for amplification of the genetic section with the genetic variation C→T at position 470 (bold face) are underlined.

FIG. 2 shows the amino acid sequence of the human EGLN2 derived from the nucleic acid sequence with the NCBI number NM_053046. The amino acid position 58 in the EGLN2 protein is in bold face.

FIG. 3 shows the amino acid sequence of the human EGLN2 variant containing a leucine at position 58. The amino acid position 58 in the EGLN2 protein is in bold face.

FIG. 4 shows the nucleic acid sequence of the human EGLN2 variant gene containing a threonine at position 470.

DESCRIPTION OF THE SEQUENCES

Figure 5:
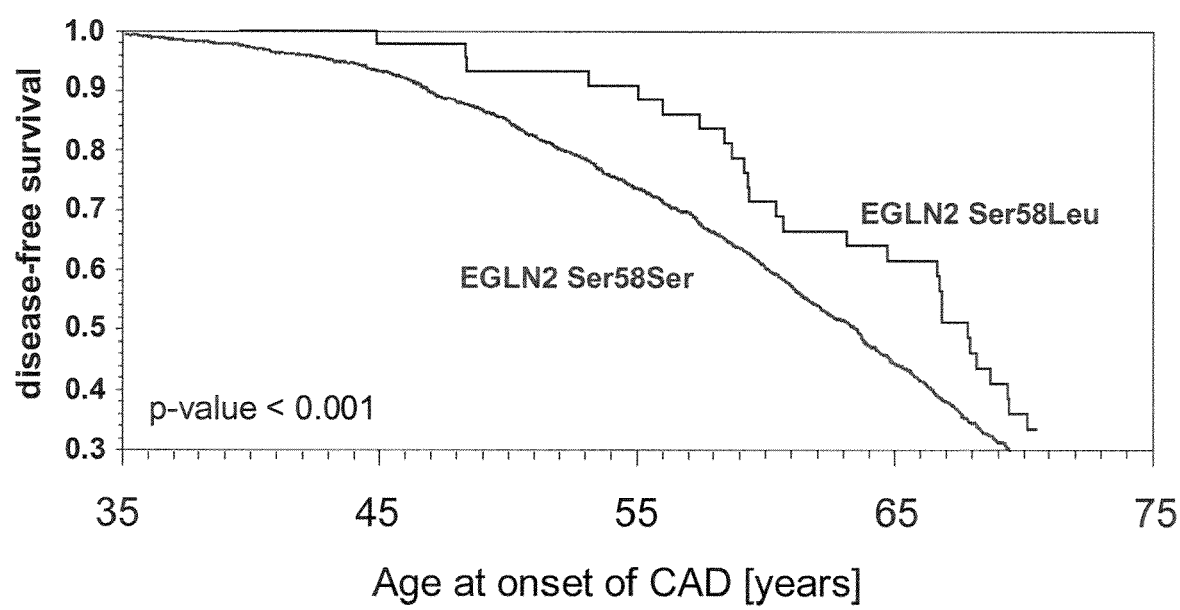
FIG. 5 shows the influence of the genotype of EGLN2 at position 470 of the reference sequence NM_053042.2, leading to amino acid exchanges at position 58 of the EGLN2 protein, on the age of the occurrence of coronary heart diseases in the patients group. P-values less than 0.05 are statistically relevant.

SEQ ID NO: 1 shows the nucleic acid sequence of the human EGLN2 protein with the NCBI number NM_053046.

SEQ ID NO: 2 shows the amino acid sequence of the human EGLN2 derived from the nucleic acid sequence with the NCBI number NM_053046.

SEQ ID NO: 3 shows the amino acid sequence of the human EGLN2 variant containing a leucine at position 58.

SEQ ID NO: 4 shows the nucleic acid sequence of the human EGLN2 variant gene containing a threonine at position 470.

SEQ ID NO 5: shows the first primer sequence of nucleotides 444-463 of the reference sequence NM_053046.2.

SEQ ID NO 6: shows the second primer sequence of complementary sequence of bases 504-521 of the reference sequence NM_053046.2.

EXAMPLES

SNP Detection by Sequencing and Analysis

Oligonucleotides (Primers) for Amplification:

The following primers were used for the detection of the nucleotide exchange from C to T at position 470 in the EGLN2 sequence with the reference number NM_053046.2:

```
Primer 1: 5'-CTGTCCAGGAGTGCCTAGTG-3'
(nucleotides 444-463 of the reference
sequence NM_053046.2; SEQ ID NO: 5);

Primer 2: 5'-GGGCTGGCAGTGGTAGAG-3'
(complementary sequence of bases
504-521 of the reference sequence
NM_053046.2; SEQ ID NO: 6).
```

PCR Protocol for Amplification:

The reagents used were from Applied Biosystems (Foster City, USA): 20 ng of genomic DNA; 1 unit TaqGold DNA polymerase; 1× Taq polymerase buffer; 500 µM dNTPs; 2.5 mM MgCl$_2$; 200 nM of each amplification primer pair as shown above; H$_2$O ad 5 µl.

Amplification Program of the PCR for Genotyping:

| | |
|---|---|
| 95° C. for 10 min | ×1 cycle |
| 95° C. for 30 sec | |
| 70° C. for 30 sec | ×2 cycles; |
| 95° C. for 30 sec | |
| 65° C. for 30 sec | ×2 cycles; |
| 95° C. for 30 sec | |
| 60° C. for 30 sec | ×2 cycles; |
| 95° C. for 30 sec | |
| 56° C. for 30 sec | |
| 72° C. for 30 sec | ×40 cycles; |
| 72° C. for 10 min | |
| 4° C. for 30 sec | ×1 cycle; |

Protocol for Minisequencing and Detection of SNPs

The reagents used were from Applied Biosystems (Foster City, USA). 2 µl purified PCR product, 1.5 µl BigDye-Terminator-Kit, 200 nM of a sequencing primer as shown above; H$_2$O ad 10 µl.

Amplification Program for Sequencing:

| | |
|---|---|
| 96° C. for 2 min | ×1 cycle; |
| 96° C. for 10 sec | |
| 55° C. for 10 sec | |
| 65° C. for 4 min | ×30 cycles; |
| 72° C. for 7 min | |
| 4° C. for 30 sec | ×1 cycle; |

Analyse of the Sequencing Products:

The sequences were analysed with the Sequenz Analyse Software (Applied Biosystems, Foster City, USA) for obtaining preliminary data first, then processed with the software Phred, Phrap, Polyphred und Consed. Phred, Phrap, Polyphred und Consed, written by Phil Green of the Washington University (world wide web at genome dot Washington dot edu).

Results

Characteristics of the Group of Persons

Table 1 shows the characteristics of the group of persons studied.

TABLE 1

| | | n | % |
|---|---|---|---|
| Total | | 2074 | |
| Sex | Female | 603 | 29.07 |
| | Male | 1471 | 70.93 |
| Age | | 61.8 (+/−10.5) | |
| BMI (Body Mass Index) | | 29.1 (+/−4.4) | |
| Blood Preasure | | 1214 | 58.7 |
| Smoker | | 1372 | 66.41 |
| Typ II Diabetis | | 361 | 17.46 |
| Myocardial infarction | | 830 | 40.59 |
| Stroke | | 145 | 7.01 |

Frequence and Distribution of the Variants of the EGLN2 Gene

Table 2 shows the frequency and distribution of the genetic variants of the EGLN2 gene at position 470 of the reference sequence NM_053046.2 in the patient group studied.

TABLE 2

| | Frequency | Percentage |
|---|---|---|
| EGNL2-C470C (EGNL2 Ser58Ser) | 1253 | 96.31 |
| EGNL2-C470T (EGNL2 Ser58Leu) | 47 | 3.61 |
| EGNL2-T470T (EGNL2 Leu58Leu) | 1 | 0.08 |
| Missing values | 773 | |

In the following only individuals with EGLN2-C470C (EGLN2 Ser58Ser) and EGLN2-C470T (EGLN2 Ser58Leu) are taken into account.

Influence of the Variants of EGLN2 on the Occurrence of Early Myocardial Infarction Table 3 shows the influence of the genotype of EGLN2 at position 470 of the reference sequence NM_053046.2 on the occurrence of early myocardial infarction (less than 55 years old for men and less than 60 years old for women) and of stroke/PRIND (prolonged reversible ischemic neurological deficit)/TIA (transitoric ischemic attack) in the patient group studied. P-values less than 0.05 are statistically relevant.

TABLE 3

| | EGLN2 | | |
|---|---|---|---|
| Clinical Parameter | C470C/ Ser58Ser n (%) | C470T/ Ser58Leu n (%) | p-value |
| Patients with early myocardial infarction (<55m/60f) | 215 (17.16) | 2 (4.26%) | 0.0199 |
| Patients without early myocardial infarction (<55m/60f) | 1038 (82.84) | 45 (95.74) | |
| Patients with Stroke/PRIND/TIA | 88 (7.23) | 7 (14.89) | 0.0418 |
| Patients without Stroke/PRIND/TIA | 1165 (92.77) | 40 (85.11) | |

Results:
1. The patients with EGLN2-C470C showed a statistically higher incidence for early myocardial infarction compared to patients with EGLN2-C470T.
2. The patients with EGLN2-C470T showed a significant increase of the risk to receive a stroke, PRIND and/or TIA compared with patients with EGLN2-C470C.

Influence of the Variants of EGLN2 on Patients' Age with Coronary Heart Diseases FIG. 5 shows the influence of the genotype of EGLN2 at position 470 of the reference sequence NM_053042.2 on the age of the occurrence of coronary heart diseases in the patients group.

Result:

A significant dependency of the age of the patients with EGLN2-C470C (EGLN2 Ser58Ser) for the early occurrence of coronary heart diseases was discovered compared to the age of patients with EGLN2-C470T (EGLN2 Ser58Leu).

CONCLUSION

The statistically significant associations between the genetic variants of the gene coding for EGLN2 and/or the protein EGLN2 shown above are a clear indication for the involvement of said genetic variants in the occurrence of thrombotic and/or coronary heart diseases. Consequently, said genetic variants are biological markers for the prognosis of thrombotic and/or coronary heart diseases, in particular for the prognosis of early myocardial infarction and/or stroke, PRIND and/or TIA.

We claim:

1. A method of screening for a modulator of an Egl Nine homolog 2 (EGLN2) protein comprising the amino acid sequence of SEQ ID NO: 3, wherein the method comprises the steps of:
   (a) providing the EGLN2 protein of SEQ ID NO: 3 or a host cell comprising a nucleic acid coding said EGLN2 protein,
   (b) providing a test compound, and
   (c) measuring or detecting the influence of the test compound on said EGLN2 protein or the EGLN2 gene encoding the same.

2. The method according to claim 1, wherein the test compound is provided in the form of a chemical compound library.

3. The method according to claim 1, wherein the influence of the test compound on the EGLN2 protein or the EGLN2 gene is measured or detected in a heterogeneous or homogeneous assay.

4. The method according to claim 1, wherein the method is carried out on an array.

5. The method according to claim 1, wherein the method is carried out using whole cells.

6. The method according to claim 1, wherein the method is carried out in a robotics system.

7. The method according to claim 1, wherein the method is carried out using microfluidics.

8. The method according to claim 1, wherein the method is a method of high-throughput screening.

9. A method for producing a medicament for the treatment of thromboembolic and/or coronary heart diseases, wherein the method comprises the steps of:
   (a) carrying out the method according to claim 1,
   (b) isolating a measured or detected test compound suitable for the treatment of a thromboembolic and/or coronary heart disease, and
   (c) formulating the measured or detected test compounds with one or more pharmaceutically acceptable carriers or auxiliary substances.

* * * * *

SEQUENCE LISTING

<160> NUMBER OF SEQ ID NOS: 6

<210> SEQ ID NO 1
<211> LENGTH: 2111
<212> TYPE: DNA
<213> ORGANISM: Homo sapiens

<400> SEQUENCE: 1

```
gctttcccct gcctgcctgt ctctagtttc tctcacatcc cttttttttt ttcctttctc      60
tagccaccct gaagggtccc ttcccaagcc cttagggacc gcagaggact tggggaccag     120
caagcaaccc ccagggcacg agaagagctc ttgctgtctg ccctgcctca ccctgcccca     180
cgccaggccc ggtggccccc agctgcatca agtggaggcg gaggaggagg cggaggaggg     240
tggcaccatg ggcccgggcg gtgccctcca tgcccggggg atgaagacac tgctgccatg     300
gacagcccgt gccagccgca gcccctaagt caggctctcc ctcagttacc agggtcttcg     360
tcagagccct tggagcctga gcctggccgg gccaggatgg gagtggagag ttacctgccc     420
tgtcccctgc tcccctccta ccactgtcca ggagtgccta gtgaggcctc ggcagggagt     480
gggacccca gagccacagc cacctctacc actgccagcc tcttcggga cggttttggc     540
gggcaggatg gtggtgagct gcggccgctg cagagtgaag gcgctgcagc gctggtcacc     600
aaggggtgcc agcgattggc agcccagggc gcacggcctg aggcccccaa acggaaatgg     660
gccgaggatg gtgggatgc cccttcaccc agcaaacggc cctgggccag caagagaac      720
caggaggcag agcgggaggg tggcatgagc tgcagctgca gcagtggcag tggtgaggcc     780
agtgctgggc tgatggagga ggcgctgccc tctgcgcccg agcgcctggc cctggactat     840
atcgtgccct gcatgcggta ctacggcatc tgcgtcaagg acagcttcct gggggcagca     900
ctgggcggtc gcgtgctggc cgaggtggag gccctcaaac ggggtgggcg cctgcgagac     960
gggcagctag tgagccagag ggcgatcccg ccgcgcagca tccgtgggga ccagattgcc    1020
tgggtggaag gccatgaacc aggctgtcga agcattggtg ccctcatggc ccatgtggac    1080
gccgtcatcc gccactgcgc agggcggctg ggcagctatg tcatcaacgg cgcgcaccaag   1140
gccatggtgg cgtgttaccc aggcaacggg ctcgggtacg taaggcacgt tgacaatccc    1200
cacggcgatg ggcgctgcat cacctgtatc tattacctga atcagaactg ggacgttaag    1260
gtgcatggcg gcctgctgca gatcttccct gagggccggc ccgtggtagc caacatcgag    1320
ccactctttg accggttgct catttttctgg tctgaccggc ggaaccccca cgaggtgaag    1380
ccagcctatg ccaccaggta cgccatcact gtctggtatt ttgatgccaa ggagcgggca    1440
gcagccaaag acaagtatca gctagcatca ggacagaaag gtgtccaagt acctgtatca    1500
cagccgccta cgcccaccta gtggccagtc ccagagccgc atggcagaca gcttaaatga    1560
cttcaggaga gccctgggcc tgtgctggct gctccttccc tgccaccgct gctgcttctg    1620
actttgcctc tgtcctgcct ggtgtggagg gctctgtctg ttgctgagga ccaaggagga    1680
gaagagacct ttgctgcccc atcatggggg ctggggttgt cacctggaca ggggcagcc    1740
gtggaggcca ccgttaccaa ctgaagctgg gggcctgggt cctaccctgt ctggtcatga    1800
ccccattagg tatggagagc tgggaggagg cattgtcact tcccaccagg atgcaggact    1860
tggggttgag gtgagtcatg gcctcttgct ggcaatgggg tgggaggagt accccaagt     1920
cctctcactc ctccagcctg gaatgtgaag tgactcccca accccttttgg ccatggcagg    1980
cacctttttgg actgggctgc cactgcttgg gcagagtaaa aggtgccagg aggagcatgg    2040
gtgtggaagt cctgtcagcc aagaaataaa agtttacctc agagctgcaa aaaaaaaaa     2100
aaaaaaaaaa a                                                          2111
```

<210> SEQ ID NO 2
<211> LENGTH: 407
<212> TYPE: PRT
<213> ORGANISM: Homo sapiens

```
<400> SEQUENCE: 2

Met Asp Ser Pro Cys Gln Pro Gln Pro Leu Ser Gln Ala Leu Pro Gln
1               5                   10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Leu Pro Ser Tyr
                35                  40                  45

His Cys Pro Gly Val Pro Ser Glu Ala Ser Ala Gly Ser Gly Thr Pro
    50                  55                  60

Arg Ala Thr Ala Thr Ser Thr Thr Ala Ser Pro Leu Arg Asp Gly Phe
65                  70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
                100                 105                 110

Arg Pro Glu Ala Pro Lys Arg Lys Trp Ala Glu Asp Gly Gly Asp Ala
            115                 120                 125

Pro Ser Pro Ser Lys Arg Pro Trp Ala Arg Gln Glu Asn Gln Glu Ala
130                 135                 140

Glu Arg Glu Gly Gly Met Ser Cys Ser Cys Ser Ser Gly Ser Gly Glu
145                 150                 155                 160

Ala Ser Ala Gly Leu Met Glu Ala Leu Pro Ser Ala Pro Glu Arg
                165                 170                 175

Leu Ala Leu Asp Tyr Ile Val Pro Cys Met Arg Tyr Tyr Gly Ile Cys
                180                 185                 190

Val Lys Asp Ser Phe Leu Gly Ala Ala Leu Gly Gly Arg Val Leu Ala
            195                 200                 205

Glu Val Glu Ala Leu Lys Arg Gly Gly Arg Leu Arg Asp Gly Gln Leu
            210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
                260                 265                 270

Ser Tyr Val Ile Asn Gly Arg Thr Lys Ala Met Val Ala Cys Tyr Pro
        275                 280                 285

Gly Asn Gly Leu Gly Tyr Val Arg His Val Asp Asn Pro His Gly Asp
        290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
                340                 345                 350

Asp Arg Arg Asn Pro His Glu Val Lys Pro Ala Tyr Ala Thr Arg Tyr
            355                 360                 365

Ala Ile Thr Val Trp Tyr Phe Asp Ala Lys Glu Arg Ala Ala Ala Lys
        370                 375                 380

Asp Lys Tyr Gln Leu Ala Ser Gly Gln Lys Gly Val Gln Val Pro Val
385                 390                 395                 400

Ser Gln Pro Pro Thr Pro Thr
                405
```

<210> SEQ ID NO 3
<211> LENGTH: 407
<212> TYPE: PRT
<213> ORGANISM: Homo sapiens

<400> SEQUENCE: 3

```
Met Asp Ser Pro Cys Gln Pro Gln Pro Leu Ser Gln Ala Leu Pro Gln
1               5                   10                  15

Leu Pro Gly Ser Ser Glu Pro Leu Glu Pro Gly Arg Ala
            20                  25                  30

Arg Met Gly Val Glu Ser Tyr Leu Pro Cys Pro Leu Leu Pro Ser Tyr
            35                  40                  45

His Cys Pro Gly Val Pro Ser Glu Ala Leu Ala Gly Ser Gly Thr Pro
    50                  55                  60

Arg Ala Thr Ala Thr Ser Thr Ala Ser Pro Leu Arg Asp Gly Phe
65              70                  75                  80

Gly Gly Gln Asp Gly Gly Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125

Pro Ser Pro Ser Lys Arg Pro Trp Ala Arg Gln Glu Asn Gln Glu Ala
    130                 135                 140

Glu Arg Glu Gly Gly Met Ser Cys Ser Cys Ser Ser Gly Ser Gly Glu
145                 150                 155                 160

Ala Ser Ala Gly Leu Met Glu Glu Ala Leu Pro Ser Ala Pro Glu Arg
                165                 170                 175

Leu Ala Leu Asp Tyr Ile Val Pro Cys Met Arg Tyr Tyr Gly Ile Cys
                180                 185                 190

Val Lys Asp Ser Phe Leu Gly Ala Ala Leu Gly Gly Arg Val Leu Ala
            195                 200                 205

Glu Val Glu Ala Leu Lys Arg Gly Gly Arg Leu Arg Asp Gly Gln Leu
210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
                260                 265                 270

Ser Tyr Val Ile Asn Gly Arg Thr Lys Ala Met Val Ala Cys Tyr Pro
            275                 280                 285

Gly Asn Gly Leu Gly Tyr Val Arg His Val Asp Asn Pro His Gly Asp
            290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
370                 375                 380
```

```
Asp Lys Tyr Gln Leu Ala Ser Gly Gln Lys Gly Val Gln Val Pro Val
385                 390                 395                 400

Ser Gln Pro Pro Thr Pro Thr
                405

<210> SEQ ID NO 4
<211> LENGTH: 2111
<212> TYPE: DNA
<213> ORGANISM: Homo sapiens

<400> SEQUENCE: 4
gctttcccct gcctgcctgt ctctagtttc tctcacatcc cttttttttt ttcctttctc    60
tagccaccct gaagggtccc ttcccaagcc cttagggacc gcagaggact tggggaccag   120
caagcaaccc ccagggcacg agaagagctc ttgctgtctg ccctgcctca ccctgcccca   180
cgccaggccc ggtggccccc agctgcatca agtggaggcg gaggaggagg cggaggaggg   240
tggcaccatg ggcccgggcg tgccctcca tgcccggggg atgaagacac tgctgccatg   300
gacagcccgt gccagccgca gcccctaagt caggctctcc ctcagttacc agggtcttcg   360
tcagagccct tggagcctga gcctggccgg gccaggatgg gagtggagag ttacctgccc   420
tgtcccctgc tcccctccta ccactgtcca ggagtgccta gtgaggcctt ggcagggagt   480
gggaccccca gagccacagc cacctctacc actgccagcc ctcttcggga cggttttggc   540 ggcaggatg gtggtgagct gcggccgctg cagagtgaag gcgctgcagc gctggtcacc   600 aagggggtgcc agcgattggc agcccagggc gcacggcctg aggcccccaa acggaaatgg   660
gccgaggatg gtggggatgc cccttcaccc agcaaacggc cctgggccag caagagaac   720 caggaggcag agcgggaggg tggcatgagc tgcagctgca gcagtggcag tggtgaggcc   780
agtgctgggc tgatggagga ggcgctgccc tctgcgcccg agcgcctggc cctggactat   840
atcgtgccct gcatgcggta ctacggcatc tgcgtcaagg acagcttcct gggggcagca   900
ctgggcggtc gcgtgctggc cgaggtggag gccctcaaac ggggtgggcg cctgcgagac   960
gggcagctag tgagccagag ggcgatcccg ccgcgcagca tccgtgggga ccagattgcc  1020
tgggtggaag gccatgaacc aggctgtcga agcattggtg ccctcatggc ccatgtggac  1080
gccgtcatcc gccactgcgc agggcggctg ggcagctatg tcatcaacgg cgcaccaag  1140 gccatggtgg cgtgttaccc aggcaacggg ctcgggtacg taaggcacgt tgacaatccc  1200
cacggcgatg ggcgctgcat cacctgtatc tattacctga atcagaactg ggacgttaag  1260
gtgcatggcg gcctgctgca gatcttccct gagggccggc ccgtggtagc caacatcgag  1320
ccactctttg accggttgct cattttctgg tctgaccggc ggaaccccca cgaggtgaag  1380
ccagcctatg ccaccaggta cgccatcact gtctggtatt tgatgccaa ggagcgggca  1440 gcagccaaag acaagtatca gctagcatca ggacagaaag gtgtccaagt acctgtatca  1500
cagccgccta cgcccaccta gtggccagtc ccagagccgc atgcagaca gcttaaatga  1560 cttcaggaga gccctgggcc tgtgctggct gctccttccc tgccaccgct gctgcttctg  1620
actttgcctc tgtcctgcct ggtgtggagg gctctgtctg ttgctgagga ccaaggagga  1680
gaagagacct tgctgccccc atcatggggg ctggggttgt cacctggaca ggggcagcc  1740 gtggaggcca ccgttaccaa ctgaagctgg gggcctgggt cctaccctgt ctggtcatga  1800
ccccattagg tatggagagc tgggaggagg cattgtcact tcccaccagg atgcaggact  1860
tggggttgag gtgagtcatg gcctcttgct ggcaatgggg tgggaggagt accccccaagt  1920 cctctcactc ctccagcctg gaatgtgaag tgactcccca acccctttgg ccatggcagg  1980
```

-continued

```
caccttttgg actgggctgc cactgcttgg gcagagtaaa aggtgccagg aggagcatgg    2040
gtgtggaagt cctgtcagcc aagaaataaa agtttacctc agagctgcaa aaaaaaaaaa    2100
aaaaaaaaaa a                                                         2111

<210> SEQ ID NO 5
<211> LENGTH: 20
<212> TYPE: DNA
<213> ORGANISM: artificial
<220> FEATURE:
<223> OTHER INFORMATION: Primer

<400> SEQUENCE: 5
ctgtccagga gtgcctagtg                                                20

<210> SEQ ID NO 6
<211> LENGTH: 18
<212> TYPE: DNA
<213> ORGANISM: artificial
<220> FEATURE:
<223> OTHER INFORMATION: Primer

<400> SEQUENCE: 6
gggctggcag tggtagag                                                  18
```